(12) United States Patent
Burli et al.

(10) Patent No.: US 12,001,780 B1
(45) Date of Patent: Jun. 4, 2024

(54) SYSTEMS AND METHODS TO MAINTAIN AMENDS TO AN ANNOTATION AS DISCRETE CHRONOLOGICAL EVENTS

(71) Applicant: Suki AI, Inc., Redwood City, CA (US)

(72) Inventors: Badarinarayan Parthasarathi Burli, Bengaluru (IN); Harish Chandra Thuwal, Delhi (IN); Sai Chaitanya Ramineni, Karimnagar (IN)

(73) Assignee: Suki AI, Inc., Redwood City, CA (US)

( * ) Notice: Subject to any disclaimer, the term of this patent is extended or adjusted under 35 U.S.C. 154(b) by 0 days.

(21) Appl. No.: 18/350,677

(22) Filed: Jul. 11, 2023

Related U.S. Application Data

(63) Continuation of application No. 18/072,984, filed on Dec. 1, 2022, now Pat. No. 11,734,502.

(51) Int. Cl.
*G06F 17/00* (2019.01)
*G06F 40/169* (2020.01)
*G06F 40/186* (2020.01)
*G16H 15/00* (2018.01)

(52) U.S. Cl.
CPC .......... *G06F 40/169* (2020.01); *G06F 40/186* (2020.01); *G16H 15/00* (2018.01)

(58) Field of Classification Search
CPC ...... G06F 40/169; G06F 40/186; G16H 15/00
USPC .......................................................... 715/230
See application file for complete search history.

(56) References Cited

U.S. PATENT DOCUMENTS

| | | | |
|---|---|---|---|
| 10,365,905 B1* | 7/2019 | Ong | G06F 8/433 |
| 10,871,950 B2* | 12/2020 | De Smet | G06F 16/9024 |
| 2008/0052379 A1* | 2/2008 | Matsuyama | H04L 41/22 |
| | | | 709/218 |
| 2012/0253793 A1* | 10/2012 | Ghannam | G06F 40/169 |
| | | | 704/9 |
| 2014/0143736 A1* | 5/2014 | Huang | G06Q 10/0637 |
| | | | 715/854 |
| 2016/0357720 A1* | 12/2016 | Thimbleby | G06F 3/1423 |
| 2021/0073290 A1* | 3/2021 | Hunter | G06N 3/084 |
| 2022/0391381 A1* | 12/2022 | Thimbleby | G06F 16/275 |

(Continued)

OTHER PUBLICATIONS

Ide, GrAF: A Graph-Based Format for Linguistic Annotations, Proceedings of the Linguistic Annotations Workshop, 2007 Association for Computational Linguistics 2007 (Year: 2007).*

*Primary Examiner* — Stephen S Hong
*Assistant Examiner* — Matthew J Ludwig
(74) *Attorney, Agent, or Firm* — Esplin & Associates, PC

(57) ABSTRACT

Systems and methods to maintain amends to an annotation as discrete chronological events are disclosed. Exemplary implementations may: obtain a selection of a first annotation template for a first annotation via a client computing platform; generate a root node based on the selection of the first annotation template; obtain a first command to update to the first annotation; append a first update node to the root node responsive to the first command; obtain a second command to update to the first annotation; append a second update node to the first node responsive to the second command; receive an indication to present the first annotation; generate, responsive to the indication, the first annotation by populating the first annotation template included in the root node based on the first node set and in sequential order indicated by the edges; and effectuate presentation of the first annotation.

20 Claims, 5 Drawing Sheets

(56) References Cited

U.S. PATENT DOCUMENTS

| | | | |
|---|---|---|---|
| 2023/0252006 A1* | 8/2023 | Barlew | G06F 16/213 707/807 |
| 2023/0252700 A1* | 8/2023 | Barlew | G06T 11/206 |

* cited by examiner

Clinical Note

Summary
Patient is a 51 year old male

Assessment

316a

Medications

FIG. 4C

Clinical Note

Summary
Patient is a 51 year old male

Assessment

316b

Medications

FIG. 4D

SYSTEMS AND METHODS TO MAINTAIN AMENDS TO AN ANNOTATION AS DISCRETE CHRONOLOGICAL EVENTS

FIELD OF THE DISCLOSURE

The present disclosure relates to systems and methods to maintain amends to an annotation as discrete chronological events.

BACKGROUND

Generating an annotation by using user dictation typically generates one uninterrupted transcript based on an initial uninterrupted dictation, both of which are subsequently saved in correlation, in addition to the annotation. When the user dictates an amendment to the annotation, such as adding a sentence in a section of the annotation that the user selected, the dictation and the transcript stay in chronological order where the annotation reflects the sentence in the section. Thus, the dictation and corresponding transcript of the dictation are not consistent with the annotation for reviewers to utilized for finalization of the annotation.

SUMMARY

One aspect of the present disclosure relates to a system configured to maintain amends to an annotation as discrete chronological events. As a user provide commands via user dictation or inputs to generate an annotation, a node set may be established. The node set may define the annotation and may be utilized to assemble a latest or current state of the annotation or a particular state or version of the annotation upon request. The node set may include a root node representing a template that originated the annotation, and update nodes that represent the different commands and a state or version of the annotation subsequent to the different command. The nodes are connected with edges that represent a sequence of the commands. Thus, the different chronological states or versions of the annotation subsequent to individual ones of the commands may be accessible.

The node set may enable storage of the sole individual changes to the annotation which may be utilized to generate different version of the annotation. This is an improvement to storing large amounts of duplicate information for each state, which is storage heavy. Rather, the different states or versions may be generated by selecting the update node that represents the desired state, ultimately optimizing storage and improving organization of changes to the annotation.

The system may include electronic storage, one or more hardware processors configured by machine-readable instructions, and/or other elements. The machine-readable instructions may include one or more instruction components. The instruction components may include computer program components. The instruction components may include one or more of a template selection component, a node generating component, a command obtaining component, an annotation presentation component, and/or other instruction components.

The electronic storage may store individual annotation templates, node sets that define annotations, command types input to edit individual annotations, electronic records that include information about a subject, and/or other information. The annotation templates may include the first annotation template. The individual annotation templates may include one or more sections and predefined information included in the one or more sections, and include a blank template.

The template selection component may be configured to obtain a selection of a first annotation template for a first annotation via a client computing platform.

The node generating component may be configured to generate a root node based on the selection of the first annotation template. The root node may include the first annotation template. The root node may be included in a first node set. Individual nodes included in the first node set represent a state of the first annotation.

The command obtaining component may be configured to obtain a first command to update the first annotation.

The node generating component may be configured to append a first update node to the root node responsive to the first command. The first update node may represent the first command. The first update node and the root node may be connected with a first outgoing edge. Individual edges may represent a sequence of the first node set. The edges may include outgoing edges that represent a connection between the state of the first annotation at which a given command is obtained and the given command. As such, the first outgoing edge represents a connection between the state of the first annotation at which the first command is obtained and the first command represented by the first update node.

The command obtaining component may be configured to obtain a second command to update the first annotation. The second command may be a first instance of an obtain-text command type.

The node generating component may be configured to append a second update node to the first node responsive to the second command. The second update node may represent the second command. The second update node and the first node may be connected with a second outgoing edge.

The annotation presentation component may be configured to receive an indication to present the first annotation. The annotation presentation component may be configured to generate, responsive to the indication, the first annotation by populate the first annotation template included in the root node based on the first node set and in sequential order indicated by the edges. The annotation presentation component may be configured to effectuate presentation of the first annotation.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As

BRIEF DESCRIPTION OF THE DRAWINGS

FIG. 4A-D illustrate different version of an annotation that may be generated by the system configured to maintain amends to an annotation as discrete chronological events, in accordance with one or more implementations.

DETAILED DESCRIPTION

Figure 1:
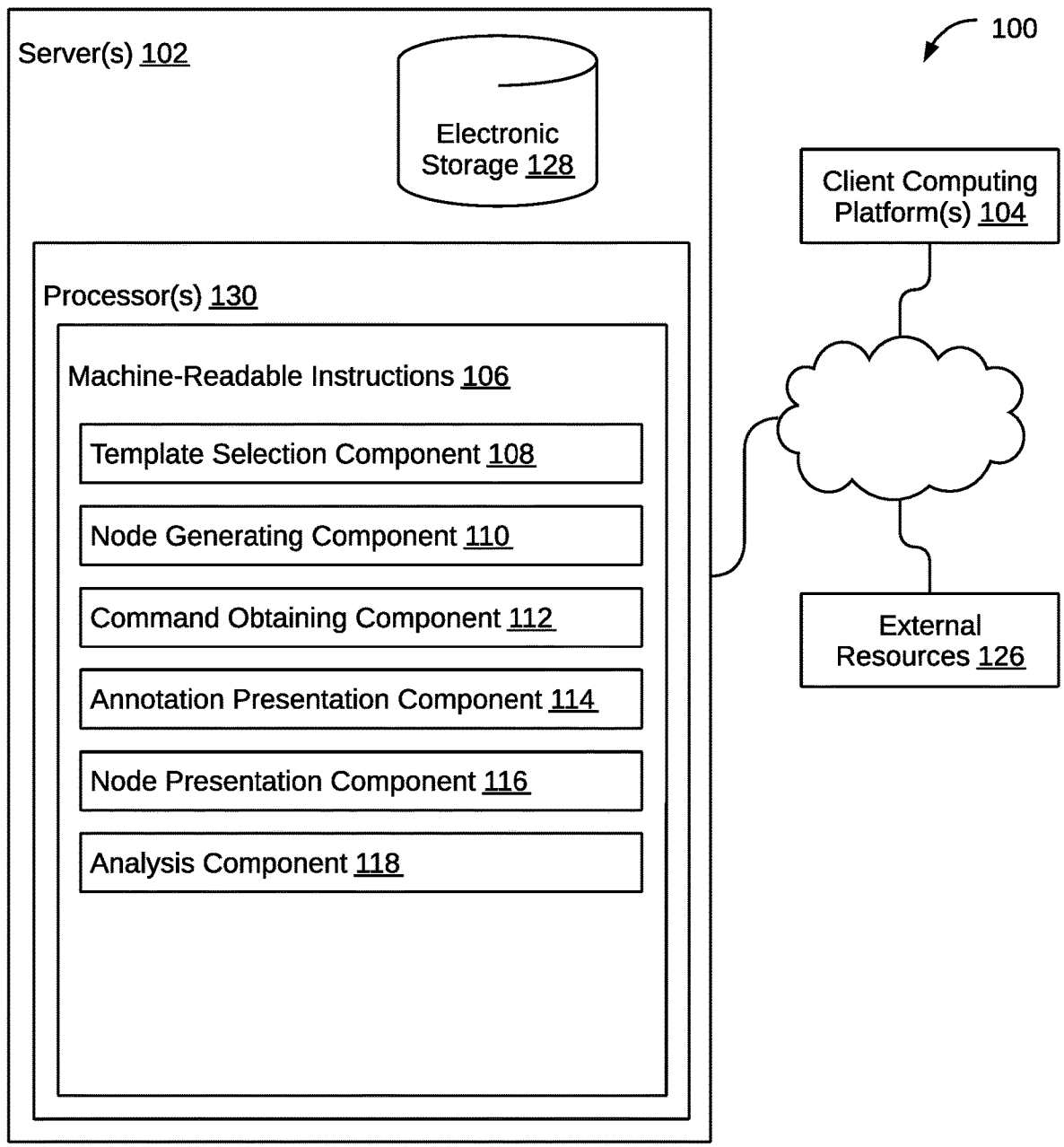
FIG. 1 illustrates a system configured to maintain amends to an annotation as discrete chronological events, in accordance with one or more implementations.

FIG. 1 illustrates a system 100 configured to maintain amends to an annotation as discrete chronological events, in accordance with one or more implementations. In some implementations, system 100 may include electronic storage 128, one or more server(s) 102, and/or other elements. Server(s) 102 may be configured to communicate with one or more client computing platform(s) 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Electronic storage 128 may store individual annotation templates including the first annotation template, node sets that define annotations, command types input by users to edit individual annotations, electronic records that include information about a subject, and/or other information. The annotation templates may include one or more predefined sections, predefined information or text, predefined information or text included in the one or more sections, and/or predefined formatting that may be utilized to add in additional information. One of the annotation templates may be blank with no sections, no predefined text, and no predefined formatting. By way of non-limiting example, the annotation templates may include a first annotation template.

The command types may be different actions that the users may initiate and implement within a given annotation to cause changes within the given annotation. The command types may be provided through user dictation, manual selections and inputs via client computing platform(s) 104, or both. The changes within the given annotation may include adding text, removing text, changing a format of specific text, and/or other changes.

The command types may include a transcribe command type, an obtain-text command type, a reformat command type, an undo command type, and/or other command types. The transcribe command type may cause determination of text based on individual instances of the transcribe command type. That is, upon a user providing an instance of the transcribe command type, e.g., the user dictating or inputting "patient is a 51 year old male", corresponding text of "patient is a 51 year old male" may be determined. In some implementations, the transcribe command type may cause determination of a transcript target position for the corresponding text based on the individual instances of the transcribe command type. The transcript target position may be where in the given annotation that the corresponding text is to be positioned or populated.

The obtain-text command type may cause identification of particular text from electronic storage 128 and/or other storage or external resources 126 based on individual instances of the obtain-text command type. The particular text, such as vitals or a history section, may be identified from the electronic records and/or other storage based on individual instances of the obtain-text command type. The electronic records may be, by way of non-limiting example, medical records, service records, order receipts, and/or other electronic records that includes information regarding one or more subjects. In some implementations, the obtain-text command type may cause determination of a text target position for the particular text identified from electronic storage 128 or other storage based on the individual instances of the obtain-text command. The text target position may be where in the given annotation that the identified text is to be positioned or populated.

The reformat command type may cause determination of particular reformatting to implement on specified text within the given annotation based on individual instances of the reformat command type. The reformatting may include color highlighting, bolding, italicizing, striking through, underlining, changing a font size, changing a font, changing line spacing, and/or reformatting. The undo command type may cause the given annotation to revert to a previous version of the same given annotation that is prior to the latest amendment made.

Obtaining the individual instances of the command types may include obtaining audio information and/or obtaining keystrokes and/or touch input via client computing platform(s) 104. The audio information may convey sounds captured by client computing platform(s) 104. The sounds may include speech dictated by the users. Speech recognition techniques may be performed on the audio information to determine text, the particular reformatting, the transcript target position, the text target position, and/or other information. The keystrokes may be provided via a physical keyboard, a virtual keyboard, and/or other device in communication with client computing platform(s) 104. The touch input may include inputs to the virtual keyboard, selections of the reformatting options, selections of sections within the annotations, selections of parameters within the annotations, selections of text within the annotations, and/or other touch inputs.

The subject of the electronic records may be, by way of non-limiting example, a patient, a vehicle, a device, a component, among others where the information included in a given electronic record is about the subject.

The node sets may be data structures that define the annotations in a sequential or chronological order that they were generated via user dictation and/or inputs. Individual node sets include a root node and one or more update nodes. The root node may include one of the annotation templates, thus representing how the given annotation originated. Individual update nodes may represent individual command instances provided (i.e., dictated or input) by the users to cause a change in the given annotation. The individual nodes may represent a state of the given annotation. The state may refer to what the first annotation may include and/or may be formatted as subsequent to the command represented by that update node.

The nodes, the root node and the one or more update nodes, may be connected with edges. Individual edges may represent a sequence of a given node set that defines the given annotation. The edges may include outgoing edges, incoming edges, and/or other edges. Individual outgoing edges may represent a connection between a given state of the given annotation at which a given command is obtained and the given command represented by a given update node. In some implementations, the outgoing edges may visually refer to an arrow from the given state pointing outward (e.g., down in a top to bottom structure, right in a left to right structure) to the given update node that represents the given command. Individual incoming edges may represent a connection between individual instances of the undo command type and a prior state of the given annotation that a latest state of the given annotation is reverting to. In some implementations, the incoming edges may visually refer to an arrow from the update node that represents an instance of the undo command type pointing inward (e.g., up in a top to bottom structure, left in a left to right structure) to a prior node.

In some implementations, individual update nodes may be associated with values to establishment parameters. By way of non-limiting example, the establishment parameters may include a node type, contains medical significance, artificial speech recognition was performed by, contains user-entered script by manual entry, contains reviewed and/or edited script by medical scribe, contains pre-filled static information, contains pre-filled dynamic information, contains information from previous annotation, contains script from artificial speech recognition that was not finalized, contains text that is formatted manually by the user, contains script that is formatted via one of the commands, contains a billable diagnostic determination, contains a non-billable diagnostic determination, contains information that is obtained from a source external to system 100 or a system that employs system 100, and/or other establishment parameters. A value to the node type is transcript or user action. The node type may be transcript upon the update node representing an instance of the transcribe command type. The node type may be user action upon the update node representing an instance of the obtain-text command type, the reformat command type, or the undo command type, or other command types.

The values to some of the establishment parameter may be binary, such as yes or no, 1 or 0, Y or N, positive or negative, among others. The value to the contain medical significance parameter may be yes upon the given annotation including information that indicates a medical implication may occur.

The value to the contain user-entered script by manual entry parameter may be yes upon the given annotation including text that a given user entered via the keystrokes as opposed to dictation.

The value to the artificial speech recognition was performed by parameter may be yes upon the given annotation including text that the given user dictated as opposed to inputting via the keystrokes.

The value to the contains pre-filled static information parameter may be yes upon the given annotation including text or information that is standard or applicable to all subjects in an annotation template.

The value to the contains pre-filled dynamic information parameter may be yes upon the given annotation including one or more parameters or other information that the given user may be required to provide values for based on the subject (e.g., weight, height, blood pressure, heart rate).

The value to the contains information from previous annotation parameter may be yes upon the given annotation including text or information that was identified and obtained from one of the annotations stored in electronic storage 128 and that is related to the subject of the given annotation.

The value to the contains script from artificial speech recognition that was not finalized parameter may be yes upon the given annotation including text that the given user dictated but was not reviewed, corrected, and/or finalized by an automatic speech recognition system, by the given user, or another user. In some implementations, the automatic speech recognition system may output intermediate text that is still in development as speech is obtained and analyzed, and final text. Thus, in some implementations, upon the automatic speech recognition system not outputting the final text, the value to the contains script from artificial speech recognition that was not finalized parameter may be yes.

The value to the contains text that is formatted manually by the user parameter may be yes upon the given annotation including text that the given user reformatted via the keystrokes and/or the touch inputs as opposed to dictation.

The value to the contains script that is formatted via one of the commands parameter may be yes upon the given annotation including upon the given annotation including text that the given user reformatted via user dictation as opposed to the keystrokes and/or the touch inputs.

In some implementations, the individual annotations may include one or more medical codes. Individual ones of the medical codes may indicate that an individual service recorded in the individual annotations is billable or non-billable to individual organizations (e.g., insurance providers). In some implementations, for example, electronic storage 128 may include one or more insurance providers that a given patient (i.e., the subject of the given annotation) is covered by. Thus, in some implementations, one or more components of system 100 (e.g., analysis component 118 describe herein) may be configured to determine the one or more medical codes, the one or more organizations, e.g., the insurance providers for the subject, to determine whether the given annotation records one or more services that are billable and/or one or more services that are non-billable. The value to the contains a billable diagnostic determination parameter may be yes upon the given annotation including one or more medical codes that indicate the one or more services that are billable to one or more of the organizations.

Additionally, the value to the contains a non-billable diagnostic determination parameter may be yes upon the given annotation including one or more medical codes that indicate one or more non-billable services to one or more of the organizations.

The value to the contains information that is obtained from a source external to system 100 or the system that employs system 100 parameter may be yes upon the given annotation including text or information that was identified and obtained from one of the annotations or other sources stored external to electronic storage 128 and/or external to storage that is maintained by the same system that employs system 100, whether related to the subject of the given annotation or not.

The value to the contains reviewed and/or edited script by medical scribe parameter may be yes upon the given annotation including text that the given user dictated and was subsequently reviewed, corrected, and/or finalized by the given user or user that is a medical scribe. In some implementations, the value to such parameter may be a name and/or other identifier of the user.

Server(s) 102 may be configured by machine-readable instructions 106. Machine-readable instructions 106 may include one or more instruction components. The instruction components may include computer program components. The instruction components may include one or more of template selection component 108, node generating component 110, command obtaining component 112, annotation presentation component 114, node presentation component 116, analysis component 118, and/or other instruction components.

Template selection component 108 may be configured to obtain a selection of one of the annotation templates, such as the first annotation template, for a first annotation via client computing platform(s) 104. The first template may be blank or may include the predefined information and/or sections.

Node generating component 110 may be configured to generate a root node based on the selection of the first annotation template. The root node may include the first annotation template. The root node may be included in a first node set. The first node set may define the first annotation. Individual nodes included in the first node set represent a state of the first annotation. A current state of the first annotation, or any given annotation, may be represented by the update node that the latest edge is connected to/pointing at, or the root node itself upon nonexistence of edges.

Command obtaining component 112 may be configured to obtain a first command to update the first annotation. The first command may be a first instance of the transcribe command type. As such, a first text based on the first command may be determined, e.g., by employing speech to text techniques.

Node generating component 110 may be configured to append a first update node to the root node responsive to the first command. The first update node may represent the first command. Appending the first update node to the root node may include including the first text in the first update node. In some implementations, appending individual update nodes may include including the corresponding command in the update node. In some implementations, including a given information or a given command in a given node may refer to establishing a correlation between the given node and the given information that is stored in electronic storage 128. In some implementations, including the given information in the given node may refer to storing the given information or the given command in a same storage location as the given node in electronic storage 128. For example, appending the first update node to the root node may include including the first command in the first update node.

In some implementations, the individual update nodes may by identified by a name, a numerical identifier, a date and time, and/or other identifier. In some implementations, the users may define the name and/or the numerical identifier. In some implementations, as the update nodes are appended, the update nodes may be assigned numerical identifiers in sequential order. The date and time may be assigned in accordance with an actual date and time that the selection and the commands are provided, and thud chronologically.

Thus, the first update node and the root node may be connected with a first outgoing edge. The first outgoing edge, and other individual edges, may represent a sequence or chronological order of the first node set, which is the chronological order of generating the first annotation via the commands. As such, the first outgoing edge may represent a connection between the state of the first annotation at which the first command is obtained (i.e., the root node that includes or represents the first annotation template) and the first command represented by the first update node to change the first annotation. The individual update nodes that may follow may be appended to the update node that represents the latest or current state of the given annotation.

Command obtaining component 112 may be configured to obtain a second command to update the first annotation. The second command may be a first instance of the obtain-text command type. As such, second text may be identified based on the second command.

Node generating component 110 may be configured to append a second update node to the first node responsive to the second command. The second update node may represent the second command. Appending the second update node may include including the second text identified in the second update node. The second update node and the first node may be connected with a second outgoing edge.

In some implementations, command obtaining component 112 may be configured to obtain a third command to update the first annotation. The third command may be a first instance of the reformat command type. The third command may specify the first text to reformat. Further, a first reformat may be determined based on the third command to implement on the first text.

Node generating component 110 may be configured to append a third update node to the second update node responsive to the third command. Additionally, the first reformat and the first text may be included in the third update node. The third update node may represent the third command. The third update node and the second update node may be connected with a third outgoing edge.

Command obtaining component 112 may be configured to obtain a fourth command to update the first annotation. The fourth command may be a first instance of the undo command type. As such, the current state of the first annotation may revert to the state represented by the second update node. That is, the current state of the first annotation may revert to, and the update node representing the fourth command may point to, the update node that precedes the state at which the fourth command was provided, i.e., the current state of the first annotation (i.e., the third update node).

Node generating component 110 may be configured to append a fourth update node to the third node responsive to the fourth command. The fourth update node may represent the fourth command. The fourth update node and the third node may be connected with a fourth outgoing edge. Appending the fourth update node may include connecting the fourth update node and the second update node with a first incoming edge, thus representing the reversion. The first incoming edge may represent a connection between the fourth update node (and the fourth command) and a prior state of the first annotation, i.e., the state of the first annotation represented by the second update node, that the current state is reverting to. A command provided subsequent to an instance of the undo command type may cause appendage of an update node (e.g., fifth update node) to the update node that represents the latest or current state of the given annotation (e.g., the second update node).

The update nodes and the edges described herein are for illustrative purposes and are not intended to be limited to a particular order as the node sets may be different from others based on instances of the command types provided by the users via the user dictations and/or inputs. In some implementations, additional instances of the command types may be provided by one or more of the users via the user dictations and/or inputs at different times so that the first annotation may be further changed. Such other user dictations and/or inputs may cause appendage of additional update nodes that correspond to the additional instances of the command types and connections between the additional update nodes with appropriate edges based on the command types, as described herein.

In some implementations, simultaneous to the generation of the root node and the appendage of the individual update nodes, corresponding population of a selected template, population of information (e.g., text obtained, transcripts of dictations), effectuation of reformatting, and effectuation of undoing/reversion may be presented via client computing platform(s) 104.

Annotation presentation component 114 may be configured to receive an indication to present a particular annotation, such as the first annotation. The indication may be received from client computing platform(s) 104 of a given user. The indication may be a request by the given user to view the particular annotation and thus assemble the particular annotation in accordance with its node set. Responsive to the indication, annotation presentation component 114 may be configured to generate the first annotation by populating the first annotation template included in the root node based on the first node set and in sequential/chronological order indicated by the edges. For example, generating the first annotation may include populating the first annotation template with the first text as required by the first command. Subsequently, generating the first annotation may include populating the first annotation template with the second text as required by the second command. Furthermore, generating the first annotation may include implementing the first reformat to the first text as required by the third command. Subsequently, generating the first annotation may include reverting the current state of the first annotation to the state of the first annotation represented by the second update node as required by the fourth command, i.e., undoing the first reformat.

Annotation presentation component 114 may be configured to effectuate presentation of the first annotation generated. The first annotation may be presented via client computing platform(s) 104 of the given user that provided the indication.

In some implementations, node presentation component 116 may be configured to receive an indication to view the first node set. That is, the indication may represent a request to view the nodes included in the first node set connected with the edges. Node presentation component 116 may be configured to generate, responsive to the indication to view the first node set, a representation of the first node set. That is, the representation may include the root node and the first update node, the second update node, the third update node, the fourth update node, and/or other update nodes included in the first node set that are connected by the edges, outgoing and incoming, in sequential order as established during the user dictation and/or inputs that provide the instances of the command types. Node presentation component 116 may be configured to effectuate presentation of the representation of the first node set.

In some implementations, the indication to present the first annotation may specify one of the update nodes that represents a particular state of the first annotation, and thus a particular version of the first annotation to present. In some implementations, one of the update nodes may be specified by the particular user selecting one of the update nodes of the presented first node set. In some implementations, one of the update nodes may be specified by the particular user dictating the name of the update node, the numerical identifier of the update node, the date and time of the update node, and/or other identifier.

In some implementations, analysis component 118 may be configured to perform analysis on the node sets, including the first node set, for example. The analysis of the update nodes of the first node set may include employing natural language processing techniques. The natural language processing techniques may include, by way of non-limiting example, sentiment analysis, named entity recognition, summarization, topic modeling, text classification, keyword extraction, lemmatization and stemming, and/or other novel or known natural language processing techniques. The values to the establishment parameters may be defined based on the analysis of individual instances of the command types that are the basis of the node sets.

The analysis may include determining similarities between individual update nodes of the first node set and other update nodes of other ones of the node sets, determining similarities between the individual node sets, determining substantive differences between one of the templates that the root nodes of the node sets include and the annotations generated based on the node sets (e.g., substantive difference between the first annotation template that the root node includes and the first annotation generated), determining reoccurrence of subsets of the node sets (e.g., a subset of the first node set) with respect to the other node sets, determining the one or more medical codes, determining the one or more organizations (e.g., the insurance providers for the subject), determining whether the given annotation records one or more services that are billable and/or one or more services that are non-billable based on the one or more medical codes and the one or more organizations, and/or other analysis.

The similarities between individual update nodes may include similar sentences and/or phrases input, a same transcript target position within the annotations (e.g., within a particular section) that the similar sentences and/or phrases are added to, similar information or text identified from electronic storage 128 to be added in the annotations, a same text target position within the annotations that the similar information or text is added to, similar reformatting of a particular sections or particular information (e.g., a particular parameter), and/or other similarities between individual update nodes. These similarities determined based on the analysis may be utilized to enhance conciseness of the representations of the individual node sets.

The similarities between the individual node sets may include a similar sequential order of similar instances of command types. The substantive differences between, for example, the first annotation template that the root node includes and the first annotation generated may include information that includes more details than the predefined information. The reoccurrence of subsets of the node sets may refer to subsets of similar instances of command types that multiple ones of the node sets include. For example, instances of the obtain-text command type to populate a general description (e.g., generally healthy patient description) and subsequently populate general informative information (e.g., recommended servings of fruits and vegetables) may be a determined subset that has reoccurred.

In some implementations, the analysis may facilitate determining and presenting suggestions via client computing platform(s) 104 while the users are providing instances of the command types to cause changes to or generate the individual annotations. Employment of the suggestions, via dictation or selection, may cause the corresponding update nodes and edges to be appended the appropriate node set.

Figure 3:
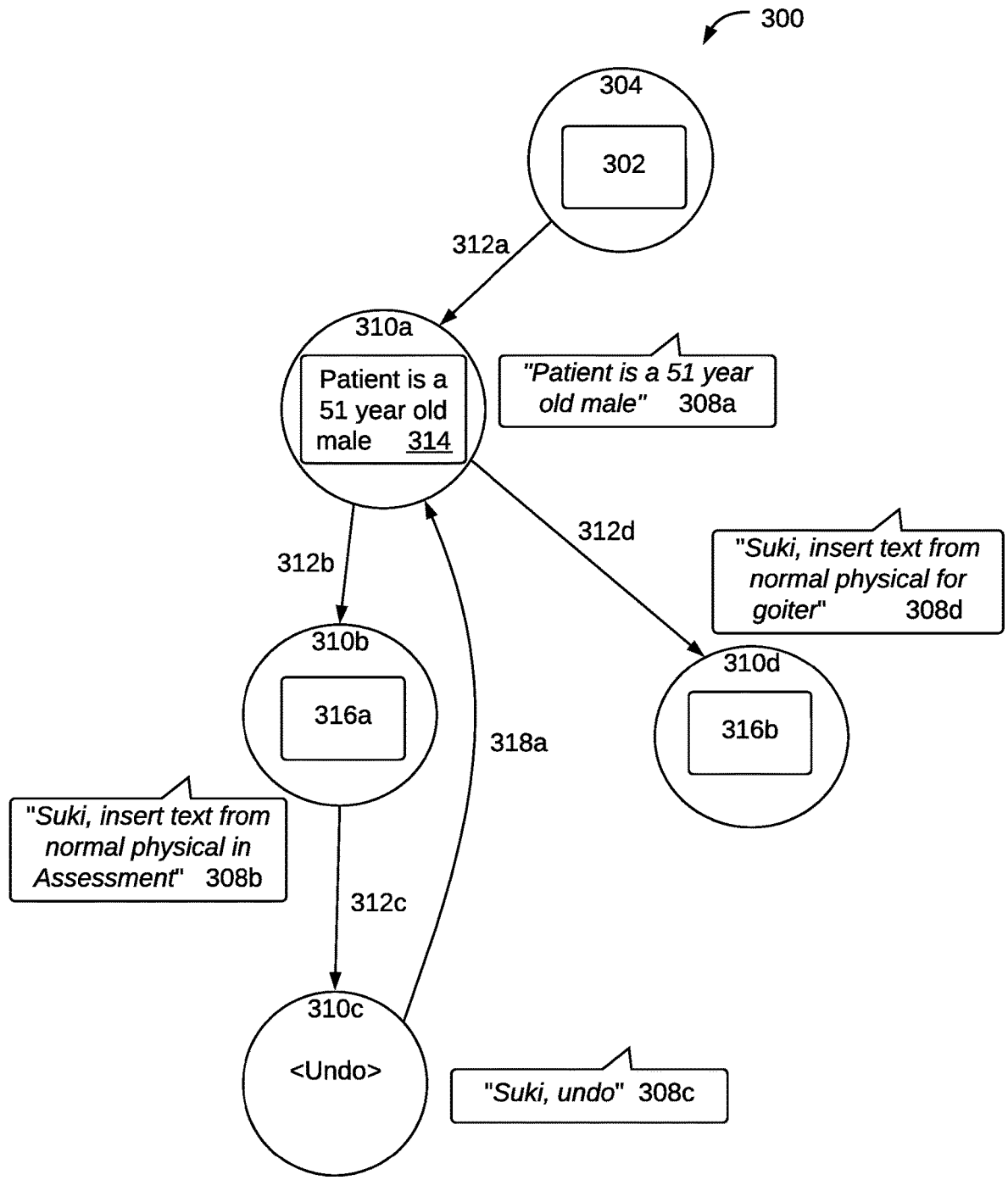
FIG. 3 illustrates an example implementation of a node set generated by the system configured to maintain amends to an annotation as discrete chronological events, in accordance with one or more implementations.
Figure 4A:
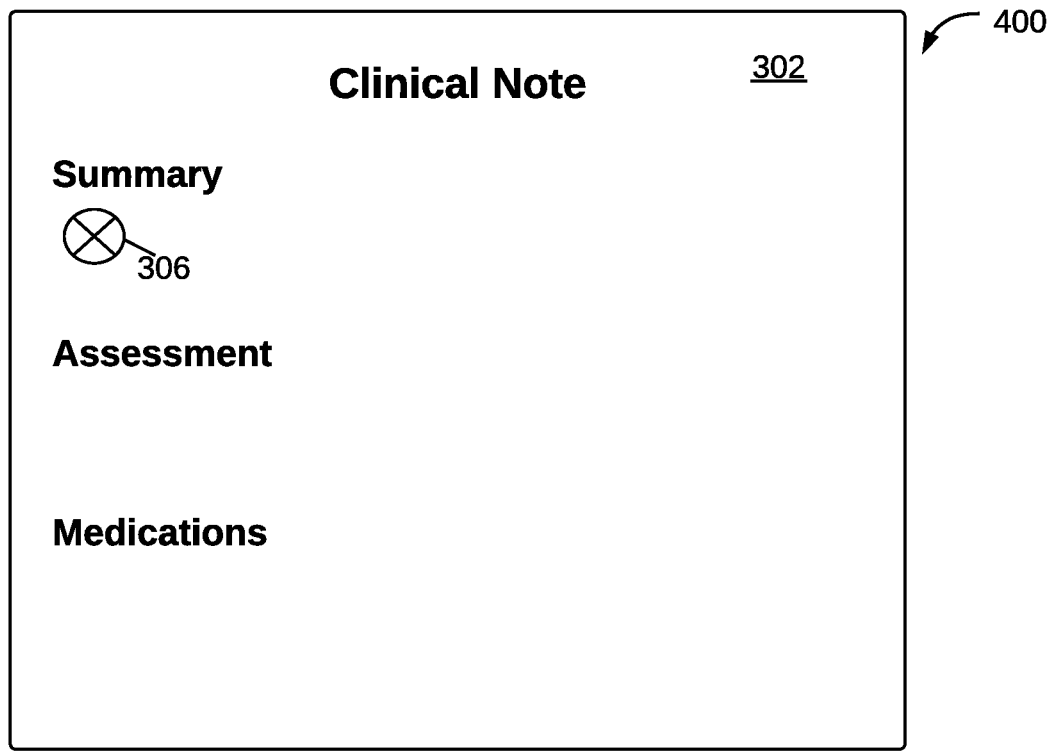
Figure 4B:
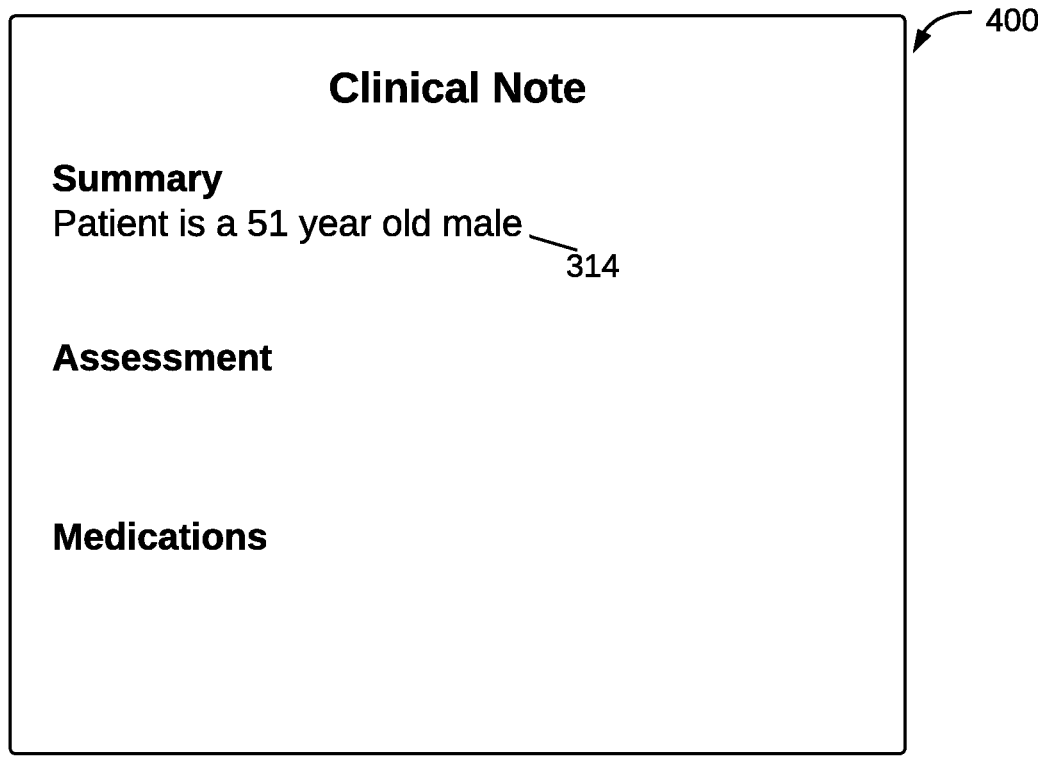

FIG. 3 illustrates a node set 300 that defines an annotation 400 in FIG. 4A-D. FIG. 4A-D illustrate different versions of annotation 400 at different states responsive to commands provided by a user. The user (not illustrated) may select template 302 illustrated in FIG. 4A for annotation 400. A root node 304 may be generated and included in node set 300 illustrated in FIG. 3. The user may select target position 306 in FIG. 4A and dictate speech 308a in FIG. 3, i.e., an instance of a transcribe command. Responsively, an update node 310a may be appended to node set 300. Root node 304 and update node 310a may be connected with an outgoing edge 312a. A text 314 corresponding to speech 308a may be determined and included in update node 310a. Simultaneously, text 314 may be populated at target position 306 such that, as illustrated in FIG. 4B, annotation 400 includes text 314 accordingly.

The user may dictate speech 308b in FIG. 3, i.e., an instance of a obtain-text command. Responsively, an update node 310b may be appended to node set 300. Update node 310a and update node 310b may be connected with an outgoing edge 312b. A text 316a may be identified and obtained, e.g., from electronic storage (not illustrated), based on speech 308b and included in update node 310b. Simultaneously, text 316a may be populated in annotation 400 such that, as illustrated in FIG. 4C, annotation 400 includes text 316a accordingly.

The user may dictate speech 308c in FIG. 3, i.e., an instance of an undo command. Responsively, an update node 310c may be appended to node set 300. Update node 310b and update node 310c may be connected with an outgoing edge 312c. Additionally, update node 310c and update node 310a may be connected with an incoming edge 318a. Thus, the latest or current state of annotation 400 is represented by update node 310a. Simultaneously, annotation 400 may revert back to annotation 400 as illustrated in FIG. 4B accordingly, which is the latest or current state of annotation 400.

The user may dictate speech 308d in FIG. 3, i.e., another instance of the obtain-text command. Responsively, an update node 310d may be appended to node set 300. Update node 310a, the latest or current state of annotation 400, and update node 310d may be connected with an outgoing edge 312d. A text 316b may be identified and obtained, e.g., from electronic storage (not illustrated), based on speech 308d and included in update node 310d. Simultaneously, text 316b may be populated in annotation 400 such that, as illustrated in FIG. 4D, annotation 400 includes text 316b accordingly.

Upon receiving an indication to view annotation 400 at a later time, annotation 400 of FIG. 4D may be generated by populating template 302 of FIG. 4A based on node set 300 in FIG. 3 in sequential order of the edges of FIG. 3.

Referring back to FIG. 1, in some implementations, server(s) 102, client computing platform(s) 104, and/or external resources 126 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 126 may be operatively linked via some other communication media.

A given client computing platform(s) 104 may include one or more processors configured to execute computer program components. The computer program components may be configured to enable an expert or user associated with the given client computing platform(s) 104 to interface with system 100 and/or external resources 126, and/or provide other functionality attributed herein to client computing platform(s) 104. By way of non-limiting example, the given client computing platform(s) 104 may include one or more of a desktop computer, a laptop computer, a handheld computer, a tablet computing platform, a NetBook, a Smartphone, a gaming console, and/or other computing platforms.

External resources 126 may include sources of information outside of system 100, external entities participating with system 100, and/or other resources. In some implementations, some or all of the functionality attributed herein to external resources 126 may be provided by resources included in system 100.

Server(s) 102 may include electronic storage 128, one or more processor(s) 130, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 128 may comprise non-transitory storage media that electronically stores information. The electronic storage media of electronic storage 128 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from server(s) 102, information received from client computing platform(s) 104, and/or other information that enables server(s) 102 to function as described herein.

Processor(s) 130 may be configured to provide information processing capabilities in server(s) 102. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 108, 110, 112, 114, 116, and/or 118, and/or other components. Processor(s) 130 may be configured to execute components 108, 110, 112, 114, 116, and/or 118, and/or other components by software; hardware; firmware; some combination of software, hardware, and/or firmware; and/or other mechanisms for configuring processing capabilities on processor(s) 130. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, 116, and/or 118 are illustrated in FIG. 1 as being implemented within a single processing unit, in implementations in which processor(s) 130 includes multiple processing units, one or more of components 108, 110, 112, 114, 116, and/or 118 may be implemented remotely from the other components. The description of the functionality provided by the different components 108, 110, 112, 114, 116, and/or 118 described below is for illustrative purposes, and is not intended to be limiting, as any of components 108, 110, 112, 114, 116, and/or 118 may provide more or less functionality than is described. For example, one or more of components 108, 110, 112, 114, 116, and/or 118 may be eliminated, and some or all of its functionality may be provided by other ones of components 108, 110, 112, 114, 116, and/or 118. As another example, processor(s) 130 may be configured to execute one or more additional components that may perform some or all of the functionality attributed below to one of components 108, 110, 112, 114, 116, and/or 118.

Figure 2:
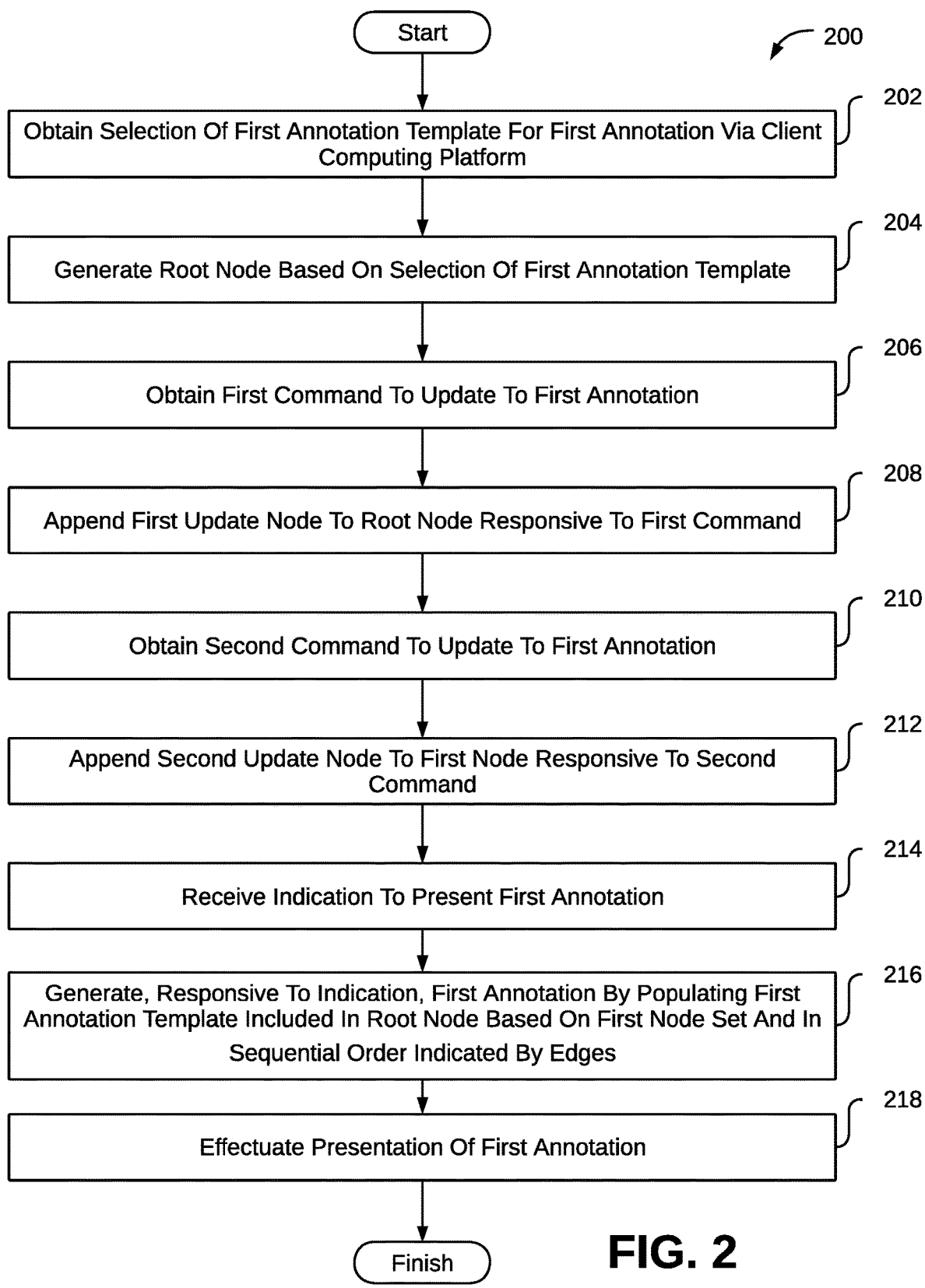
FIG. 2 illustrates a method to maintain amends to an annotation as discrete chronological events, in accordance with one or more implementations.

FIG. 2 illustrates a method 200 to maintain amends to an annotation as discrete chronological events, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining a selection of a first annotation template for a first annotation via a client computing platform. Electronic storage may store individual annotation templates including the first annotation template, node sets that define annotations, command types input to edit individual annotations, electronic records that include information about a subject, and/or other information. The individual annotation templates may include one or more sections and predefined information included in the one or more sections. Operation 202 may be performed by one or more hardware processors configured by machine-readable instructions including a component that is the same as or similar to template selection component 108, in accordance with one or more implementations.

An operation 204 may include generating a root node based on the selection of the first annotation template. The root node may include the first annotation template. The root node may be included in a first node set. Operation 204 may be performed by one or more hardware processors configured by machine-readable instructions including a component that is the same as or similar to node generating component 110, in accordance with one or more implementations.

An operation 206 may include obtaining a first command to update the first annotation. Operation 206 may be performed by one or more hardware processors configured by machine-readable instructions including a component that is the same as or similar to command obtaining component 112, in accordance with one or more implementations.

An operation 208 may include appending a first update node to the root node responsive to the first command. The first update node may represent the first command. The first update node and the root node may be connected with a first outgoing edge. Operation 208 may be performed by one or more hardware processors configured by machine-readable instructions including a component that is the same as or similar to node generating component 110, in accordance with one or more implementations.

An operation 210 may include obtaining a second command to update the first annotation. The second command may be a first instance of an obtain-text command type. Operation 210 may be performed by one or more hardware processors configured by machine-readable instructions including a component that is the same as or similar to command obtaining component 112, in accordance with one or more implementations.

An operation 212 may include appending a second update node to the first node responsive to the second command. The second update node may represent the second command. The second update node and the first node may be connected with a second outgoing edge. Operation 212 may be performed by one or more hardware processors configured by machine-readable instructions including a component that is the same as or similar to node generating component 110, in accordance with one or more implementations.

An operation 214 may include receiving an indication to present the first annotation. Operation 214 may be performed by one or more hardware processors configured by machine-readable instructions including a component that is the same as or similar to annotation presentation component 114, in accordance with one or more implementations.

An operation 216 may include generating, responsive to the indication, the first annotation by populating the first annotation template included in the root node based on the first node set and in sequential order indicated by the edges. Operation 216 may be performed by one or more hardware processors configured by machine-readable instructions including a component that is the same as or similar to annotation presentation component 114, in accordance with one or more implementations.

An operation 218 may include effectuating presentation of the first annotation. Operation 218 may be performed by one or more hardware processors configured by machine-readable instructions including a component that is the same as or similar to annotation presentation component 114, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to maintain amends to an annotation as discrete chronological events, the system comprising:

electronic storage that stores i) individual annotation templates, ii) node sets that define annotations, iii) command types input to edit individual annotations, and iv) electronic records that include information about a subject,
wherein the individual annotation templates include one or more sections and predefined information included in the one or more sections,
wherein the command types include a transcribe command type, an obtain-text command type, a reformat command type, and/or an undo command type;

one or more processors configured by machine-readable instructions to:
obtain a selection of a first annotation template for a first annotation via a client computing platform;
generate a root node based on the selection of the first annotation template, wherein the root node includes the first annotation template, wherein the root node is included in a first node set, wherein individual nodes included in the first node set represent a state of the first annotation;
obtain one or more commands to update the first annotation;
append, for each of the one or more commands, an update node to a node most recently appended to the first node set node responsive to a given command, wherein:
individual update nodes represent individual ones of the one or more commands,
the individual update nodes are connected with edges,
the edges represent a sequence of the first node set,
the individual update nodes are connected with an outgoing edge representing a connection between (ii) the given command and (ii) the state of the first annotation at which the given command is obtained upon the given command being an instance of the transcribe command type, the obtain-text command type, the reformat command type, or the undo command type,
the individual update nodes are connected with the outgoing edge and an incoming edge representing a connection between (i) the given command and (ii) a prior state of the first annotation that a current state of the first annotation is reverting back to upon the given command being the instance of the undo command type;
receive an indication to present the first annotation;
generate, responsive to the indication, the first annotation by populating the first annotation template included in the root node based on the first node set and in sequential order indicated by the edges; and
effectuate presentation of the first annotation.

2. The system of claim 1, wherein the transcribe command type causes determination of text based on individual instances of the transcribe command type, wherein appending the update node includes including the determined text in the update node, wherein generating the first annotation includes populating the first annotation template with the determined text.

3. The system of claim 1, wherein the obtain-text command type causes identification of particular text from the electronic storage based on individual instances of the obtain-text command type, wherein appending the update node includes including the identified text in the update node, wherein generating the first annotation includes populating the first annotation template with the identified text.

4. The system of claim 1, wherein the reformat command type causes determination of particular reformatting to implement on specified text based on individual instances of the reformat command type,
wherein generating the first annotation includes implementing the particular reformatting on the specified text in accordance with update nodes of the first node set that represent individual instance of the reformat command type.

5. The system of claim 1, wherein the undo command type causes the current state of the first annotation to revert to the state of the first annotation represented by the update node of the first node set prior to a latest update node appended.

6. The system of claim 1, wherein the one or more processors are further configured by the machine-readable instructions to:
receive an indication to view the first node set;
generate, responsive to the indication to view the first node set, a representation of the first node set such that the representation includes the root node and update nodes of the first node set are connected by the edges in sequential order; and
effectuate presentation of the representation of the first node set.

7. The system of claim 1, wherein appending individual update nodes includes including the corresponding command in the update node.

8. The system of claim 1, wherein the one or more processors are further configured by the machine-readable instructions to:
perform analysis on the first node set, wherein the analysis includes i) determining similarities between individual update nodes of the first node set and other update nodes of other ones of the node sets, ii) determining similarities between the node sets, iii) determining substantive differences between the first annotation template that the root node includes and the first annotation generated, and iv) determining reoccurrence of a subset of the first node set with respect to the other node sets.

9. The system of claim 8, wherein the analysis of the update nodes of the first node set includes employing natural language processing techniques.

10. The system of claim 1, wherein individual update nodes are associated with values to establishment parameters, wherein the values to the establishment parameters are defined based on the analysis of individual instances of the command types, wherein the establishment parameters include a node type, contains medical significance, artificial speech recognition was performed by, contains user-entered script by manual entry, contains reviewed and/or edited script by medical scribe, contains pre-filled static information, contains pre-filled dynamic information, contains information from previous annotation, contains script from artificial speech recognition that was not finalized, contains text that is formatted manually by the user, contains script that is formatted via one of the commands, contains a billable diagnostic determination, contains a non-billable diagnostic determination, and contains information that is obtained from a source external to the annotation, wherein a value to the node type is transcript or user action.

11. A method to maintain amends to an annotation as discrete chronological events, the method comprising:

obtaining a selection of a first annotation template for a first annotation via a client computing platform, wherein electronic storage stores i) individual annotation templates including the first annotation template, ii) node sets that define annotations, iii) command types input to edit individual annotations, and iv) electronic records that include information about a subject, wherein the individual annotation templates include one or more sections and predefined information included in the one or more sections, wherein the command types include a transcribe command type, an obtain-text command type, a reformat command type, and/or an undo command type;

generating a root node based on the selection of the first annotation template, wherein the root node includes the first annotation template, wherein the root node is included in a first node set, wherein individual nodes included in the first node set represent a state of the first annotation;

obtaining one or more commands to update the first annotation;

appending, for each of the one or more commands, an update node to a node most recently appended to the first node set node responsive to a given command, wherein:

individual update nodes represent individual ones of the one or more commands, the individual update nodes are connected with edges, the edges represent a sequence of the first node set, the individual update nodes are connected with an outgoing edge representing a connection between (ii) the given command and (ii) the state of the first annotation at which the given command is obtained upon the given command being an instance of the transcribe command type, the obtain-text command type, the reformat command type, or the undo command type, the individual update nodes are connected with the outgoing edge and an incoming edge representing a connection between (i) the given command and (ii) a prior state of the first annotation that a current state of the first annotation is reverting back to upon the given command being the instance of the undo command type;

receiving an indication to present the first annotation;

generating, responsive to the indication, the first annotation by populating the first annotation template included in the root node based on the first node set and in sequential order indicated by the edges; and effectuating presentation of the first annotation.

12. The method of claim 11, wherein the transcribe command type causes determination of text based on individual instances of the transcribe command type, wherein appending the update node includes including the determined text in the update node, wherein generating the first annotation includes populating the first annotation template with the determined text.

13. The method of claim 11, wherein the obtain-text command type causes identification of particular text from the electronic storage based on individual instances of the obtain-text command type, wherein appending the update node includes including the identified text in the update node, wherein generating the first annotation includes populating the first annotation template with the identified text.

14. The method of claim 11, wherein the reformat command type causes determination of particular reformatting to implement on specified text based on individual instances of the reformat command type, wherein generating the first annotation includes implementing the particular reformatting on the specified text in accordance with update nodes of the first node set that represent individual instance of the reformat command type.

15. The method of claim 11, wherein the undo command type causes the current state of the first annotation to revert to the state of the first annotation represented by the update node of the first node set prior to a latest update node appended.

16. The method of claim 11, further comprising:

receiving an indication to view the first node set;

generating, responsive to the indication to view the first node set, a representation of the first node set such that the representation includes the root node and update nodes of the first node set are connected by the edges in sequential order; and effectuate presentation of the representation of the first node set.

17. The method of claim 11, wherein appending individual update nodes includes including the corresponding command in the update node.

18. The method of claim 11, further comprising:

performing analysis on the first node set, wherein the analysis includes i) determining similarities between individual update nodes of the first node set and other update nodes of other ones of the node sets, ii) determining similarities between the node sets, iii) determining substantive differences between the first annotation template that the root node includes and the first annotation generated, and iv) determining reoccurrence of a subset of the first node set with respect to the other node sets.

19. The method of claim 18, wherein the analysis of the update nodes of the first node set includes employing natural language processing techniques.

20. The method of claim 11, wherein individual update nodes are associated with values to establishment parameters, wherein the values to the establishment parameters are defined based on the analysis of individual instances of the command types, wherein the establishment parameters include a node type, contains medical significance, artificial speech recognition was performed by, contains user-entered script by manual entry, contains reviewed and/or edited script by medical scribe, contains pre-filled static information, contains pre-filled dynamic information, contains information from previous annotation, contains script from artificial speech recognition that was not finalized, contains text that is formatted manually by the user, contains script that is formatted via one of the commands, contains a billable diagnostic determination, contains a non-billable diagnostic determination, and contains information that is obtained from a source external to the annotation, wherein a value to the node type is transcript or user action.

* * * * *